(12) United States Patent
Colsher et al.

(10) Patent No.: US 6,194,725 B1
(45) Date of Patent: Feb. 27, 2001

(54) SPECT SYSTEM WITH REDUCED RADIUS DETECTORS

(75) Inventors: James G. Colsher, Waukesha, WI (US); Albert H. R. Lonn, Beaconsfield Bucks (GB); Carl M. Bosch, Wauwatosa, WI (US)

(73) Assignee: General Electric Company, Waukesha, WI (US)

( * ) Notice: Subject to any disclaimer, the term of this patent is extended or adjusted under 35 U.S.C. 154(b) by 0 days.

(21) Appl. No.: 09/126,824

(22) Filed: Jul. 31, 1998

(51) Int. Cl.[7] .................................................. G01T 1/166

(52) U.S. Cl. ........................ 250/363.05; 250/363.08; 378/13

(58) Field of Search .................... 250/363.05, 363.08, 250/370.09, 360.1, 363.02; 378/13, 15

(56) References Cited

U.S. PATENT DOCUMENTS 5,444,252 * 8/1995 Hug et al. .................... 250/363.08
5,866,906 * 2/1999 Jensen ........................... 250/363.05

* cited by examiner

*Primary Examiner*—Constantine Hannaher
*Assistant Examiner*—Albert Gagliardi
(74) *Attorney, Agent, or Firm*—Quarles & Brady, LLP; Christan G. Cabou

(57) ABSTRACT

An imaging system for generating SPECT images wherein first and second cameras are mounted to a gantry for rotation about an imaging axis, the cameras are positionible in an L configuration wherein their camera axis intersect at an intersection point, the cameras are mounted such that when in the L position the intersection point is further away from each of the cameras than is the rotation axis allowing the cameras to be moved radially inward with respect to the rotation axis thus reducing the degree of table movement within the imaging area required to position an object to be imaged adjacent the cameras.

20 Claims, 3 Drawing Sheets

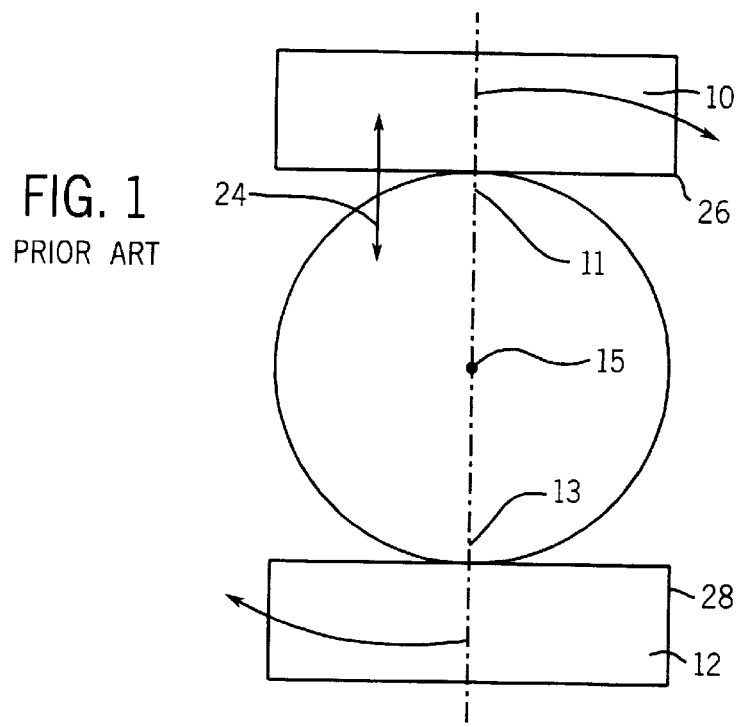
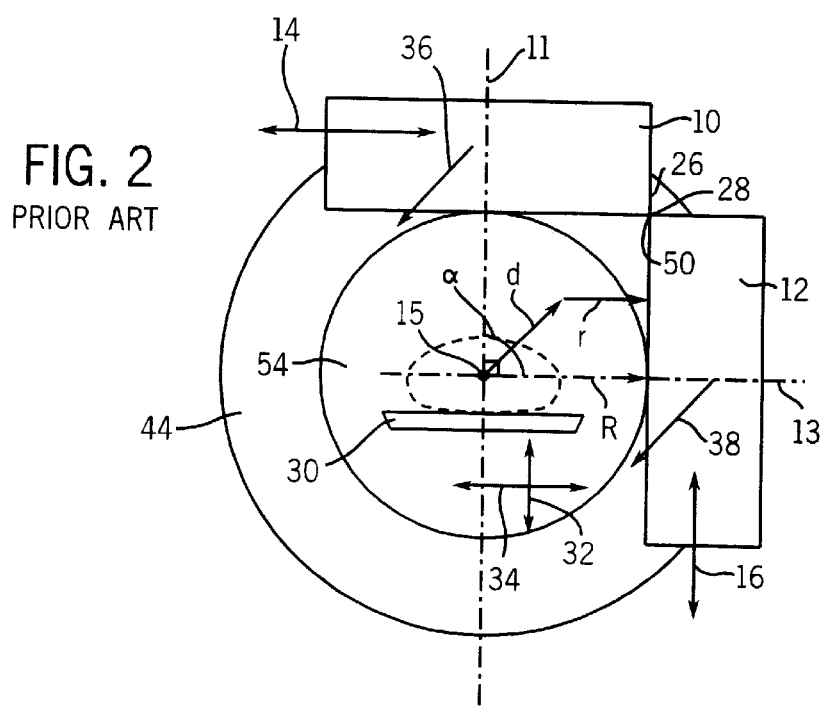

SPECT SYSTEM WITH REDUCED RADIUS DETECTORS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to single photon emission computed tomography (SPECT) and more particularly to a system or camera/gantry configuration which reduces the degree of patent support table motion required to position a patient adjacent to gamma cameras for imaging when cameras are positioned such that their axis essentially form an L.

SPECT examinations are carried out by injecting a radiopharmaceutical into the body of a patient to be examined. A radiopharmaceutical is a substance labeled with a radioisotope which emits photons at one or more energy levels. By choosing a compound which accumulates in an organ to be imaged, radiopharmaceutical concentration, and hence radioisotope concentration, can be substantially limited to an organ of interest. The organ to be imaged will be referred to hereinafter as an organ of interest and an energy range which approximates the known energy level will be referred to as the energy range.

While moving through a patient's blood stream the radiopharmaceutical becomes concentrated in the organ of interest. By measuring the number of photons emitted from the organ of interest which are within the marker range, organ characteristics, including irregularities, can be identified.

To measure the number of emitted photons planar gamma cameras are used. After a radiopharmaceutical has become concentrated within an organ of interest, a camera is positioned at an imaging angle with respect to the organ of interest such that the organ is positioned within the camera's field of view FOV. The camera is designed to detect photons traveling along preferred paths within the FOV.

A gamma camera consists of a collimator, a scintillation crystal, a plurality of photo multiplier tubes (PMTs) and a camera processor. The collimator typically includes a rectangular lead block having a width dimension and a length dimension which together define the FOV. Holes in the collimator block define the preferred photon paths. The preferred paths are unidirectional and perpendicular to the front face of the collimator. The collimator blocks emissions toward the crystal along non-preferred paths.

The scintillation crystal is positioned adjacent the collimator on a side opposite the FOV and has an impact surface and an oppositely facing emitter surface. The impact surface defines a two dimensional imaging area A having a length L and a width W. Photons which pass through the collimator are absorbed by the scintillation crystal. The crystal converts gamma photons to light photons each time a gamma photon is absorbed. The amount of light emitted depends on the absorbed photon's energy level.

The PMTs typically include between 37 and 91 PMTs which are arranged in a two dimensional array which is positioned adjacent the emitter surface. Light emitted by the crystal is detected by the PMTs which are in the area adjacent the emitter point. Each PMT which detects light generates an analog intensity signal. The intensity signal is proportional to the amount of light detected. When a single photon is absorbed by the crystal, the emitted light is typically absorbed by several different PMTs such that several PMTs generate intensity signals simultaneously. For the purposes of this explanation all intensity signals caused by a single photon will be collectively referred to as a signal set.

The processor receives each signal set and performs a plurality of calculations on each signal set to determine two characteristics of the corresponding photon. The processor combines the intensity signals of each signal set to identify the energy level of a corresponding photon. Photons having energies within the energy range will be referred to as events. Only signals corresponding to events are used for imaging. The processor also performs a series of calculations in an effort to determine precisely where in the crystal area A an event occurred. The processor uses these locations to create an image of the organ of interest which corresponds to the camera imaging angle.

To create a three dimensional "tomographic" image of the organ of interest, a gamma camera can be used to generate a plurality of images from different imaging angles. To this end, the camera is often mounted to an annular gantry and positioned parallel to, and at an imaging angle about, a rotation axis which passes through the organ of interest. The rotation angle is incremented between views so that the plurality of images are generated. The plurality of images are then used to construct pictures of transaxial slices of the torso section using algorithms and methods that are well known to those skilled in the tomographic arts.

To reduce the time required for generating a plurality of images many SPECT systems are equipped with two or more cameras which can be arranged at different angles with respect to the rotation axis. While many different two camera configurations can be formed, there are two configurations which are most widely used, an "H" configuration or mode and an "L" configuration or mode.

Referring to FIG. 1, in the H mode two cameras 10 and 12 oppose each other such that camera axis 11 and 13 are aligned and intersect an rotation axis 15. The H mode is used to image patients efficiently by acquiring two opposing views at the same time. For example, the H mode can be used to acquire two fixed views such as anterior and posterior views simultaneously. In the alternative, the H mode can be used to acquire a series of views for SPECT over 360° by acquiring images from both detectors over a 180° rotation.

Referring to FIG. 2, in the L mode the two cameras 10, 12 are positioned such that their camera axis 11, 13 intersect at rotation axis 15 forming approximately a 90 degree angle γ hence the term "L mode". In one common L mode the axis form a 90 degree angle γ while in another the axis form an essentially 101 degree angle γ. For the purposes of this explanation, although the invention can be used with any L mode configuration, in the interest of simplification, the invention will be described in the context of a 90 degree L mode unless indicated otherwise.

The L mode is typically used to image the heart. During heart imaging data is typically only collected over 180 degrees of rotation about the left side of the chest. To collect 180 degrees of data using cameras configured in the L mode, the cameras are rotated about the patient through 90 degrees, each camera separately collecting 90 degrees of imaging data for a total of 180 degrees.

Because both the L and the H modes are advantageous many SPECT systems are equipped so that two cameras can be positioned in either the H or the L mode. To this end at least one of the two system cameras is mounted such that it can be independently rotated with respect to the other system camera about the gantry, the independently moveable camera lockable in either the L or the H modes. Systems in which an operator can put the detectors in either L mode or H mode are known within the industry as "variable geometry SPECT cameras".

Because SPECT systems are expensive it is important that each system be designed such that it can be used to image virtually all patients independent of patient size. Generally, the largest section of most patients is through their chest or shoulders and is typically between 200 and 560 mm. To accommodate sections as large as 560 mm most system cameras have a field of view which is at least 540 mm. In this case, a detector enclosure or "tub" is typically over 600 mm wide.

It is well known in the industry that SPECT image quality can be improved by positioning a gamma camera as close as possible to an organ to be imaged during data gathering. To this end most SPECT systems provide some mechanism for changing the position of a patient support table relative to a gamma camera to thereby change the position of a patent on the table relative to the camera. Referring again to FIG. 1, in the H mode, one common way to change the position of a patient with respect to cameras 10 and 12 is to mount each camera 10 and 12 on a radial slide (not illustrated) which allows the cameras to be moved radially inwardly and outwardly relative to axis 15 along the direction indicated by arrow 24.

While radial slides work well in the H mode, camera geometry often prohibits radial camera motion in the L mode. Referring to FIGS. 1 and 2, to move the cameras from the H to the L mode, the cameras are first moved radially outward to a position where adjacent corners 26 and 28 will just touch in L mode. In the present example it will be assumed that this is 304 mm. Then, camera 12 is rotated about axis 15 in a counterclockwise direction toward camera 10 until adjacent edges 26 and 28 contact. In this example, edges 26 and 28 contact when the angle between axis 11 and 13 is 90 degrees. As can be seen in FIG. 2, at this point both cameras 10 and 12 cannot be moved radially inward together as the edges 26 and 28 would collide. In addition, if either camera 10 or 12 were moved inward separately, the moved camera would block a portion of the stationary camera.

Thus, in the L mode other means for changing the position of cameras 10 and 12 with respect to a patient have been developed. To this end, one way to change the position of a patient with respect to cameras 10 and 12 has been to provide an adjustable table 30 (see FIG. 2). Table 30 can move both vertically (along arrow 32) and laterally (along arrow 34) and therefore can move a patient toward both cameras 10 and 12. As cameras 10 and 12 are rotated about axis 15, table 30 moves about in a semicircular path to maintain an organ being imaged in an initial position with respect to cameras 10 and 12.

An alternative way to change the position of a patient with respect to the cameras is to mount the cameras on a gantry 44 (see FIG. 2) and move gantry 44 rather than move table 30 laterally. A configuration facilitating table horizontal and gantry lateral movement can be used together to achieve the same effective patient positioning.

Referring still to FIG. 2, the amount of table movement d required to accommodate the smallest patient having a chest diameter of 200 mm can be determined as follows. In FIG. 2, cameras 10 and 12 are in an L configuration defining a 90° angle γ. In this case the fixed radius of camera rotation about imaging axis 15 is R and the effective radius of rotation required to accommodate the smallest patient (i.e. 200 mm chest diameter) is r. Distance d can be determined by solving the following equation:

$$d = \frac{(R-r)}{\cos(\gamma/2)} \qquad \text{Eq. 1}$$

Again, assuming a fixed radius R of 304 mm and a required effective radius of 200 mm, where γ is 90°, d is 147 mm.

While adjustable tables as described above have been successfully implemented, tables required to provide necessary patient movement are relatively complex and therefore relatively expensive. This is particularly true where relatively large table movements d are required. In addition, large table movements also require a large gantry aperture as seen from FIG. 2. The gantry ring 44 prevents the patient from coming close to the cameras.

Another solution for changing the position of a patient with respect to cameras configured in the L mode has been to mount cameras to a gantry on radial/lateral slides. Referring again to FIG. 2, as above, radial slides allow cameras 10 and 12 to be moved radially with respect to axis 15. One lateral slide allows camera 10 to be moved laterally along the direction indicated by arrow 14 while another lateral slide allows camera 12 to be moved along the direction indicated by arrow 16. In this case, to move cameras 10 and 12 closer to a patient supported by table 30, camera 10 can be moved laterally away from camera 12 (i.e. in FIG. 2, to the left) and radially inward toward axis 15 while camera 12 is moved lateral away from camera 10 (i.e. in FIG. 2, downward) and radially inward toward axis 15. In effect, cameras 10 and 12 are moved in the directions indicated by arrows 36 and 38, respectively.

Unfortunately, while radial/lateral slides also have been successfully implemented, such dual motion slides, like a highly adjustable table, are also relatively complex and therefore are relatively expensive.

Therefore, it would be advantageous to have a two camera SPECT system which reduces the amount of table movement required to accommodate small patients when cameras are configured in the L mode and which does not require cameras to be mounted on lateral slides. In addition, where an adjustable table is not provided, it would be advantageous to have a SPECT system which reduces the amount of lateral slide movement required to accommodate small patients when cameras are configured in the L mode.

BRIEF SUMMARY OF THE INVENTION

The present invention includes a camera configuration which reduces the amount of table motion required to accommodate a small patient when two cameras are positioned in the L mode. To this end, the present invention requires that each of two system cameras be mounted to a gantry such that their respective camera axis are offset from the central gantry imaging axis. More specifically, the cameras are mounted on radial slides such that their camera axis intersect at an intersection point which is farther away from each of the cameras than is the gantry imaging axis. By mounting the cameras in this laterally offset fashion the cameras can be radially moved closer to a patient when in the L mode thereby reducing the amount of required table movement to accommodate a small patient.

To this end, the invention includes an imaging system for generating SPECT images, the system for use with a table positionable to support an object to be imaged within an imaging area wherein the table is capable of vertical and lateral movement to position the object within the imaging area in required positions relative to SPECT cameras. The system includes a gantry formed about a rotation axis through the imaging area and first and second cameras having first and second camera axis which pass through first and second camera fields of view, respectively. Each of the first and second cameras is mounted to the gantry for radial movement relative to the rotation axis and for rotational movement about the rotation axis.

The cameras are positionable on the gantry in at least an opposing position wherein the second camera opposes the first and an L position wherein the first and second camera axis intersect at an intersection point and essentially form an L. The cameras are mounted such that when in the L position the camera axis intersection point is further than the imaging axis from each of the cameras thereby enabling the cameras to be moved radially inwardly while still maintaining identical distances from the rotation axis.

Thus, one object of the invention is to provide a SPECT system which can be used with a relatively simple and inexpensive adjustable table. To this end, as the cameras are offset with respect to the imaging axis, the amount of table motion required to accommodate small patients is reduced. A related object is to provide a SPECT system which can be used with an inexpensive and simple adjustable table which does not require lateral camera slides.

In one embodiment, when in the L position the first and second camera axis form a 90° angle. In another embodiment the first and second camera axis form an angle other than 90° such as 101°.

Preferably, prior to imaging, when in the L position with the cameras moved into a position in which each camera is radially inward as far as possible while still maintaining identical distances between each camera and the imaging axis, a locking mechanism is provided to maintain the cameras in the L position.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

BRIEF DESCRIPTION OF THE SEVERAL VIEWS OF THE DRAWINGS

FIG. 1 is a schematic diagram illustrating two SPECT cameras position in an posing H mode;

FIG. 2 is a schematic diagram similar to FIG. 1, albeit with the camera in an adjacent L mode;

DETAILED DESCRIPTION OF THE INVENTION

Figure 3:
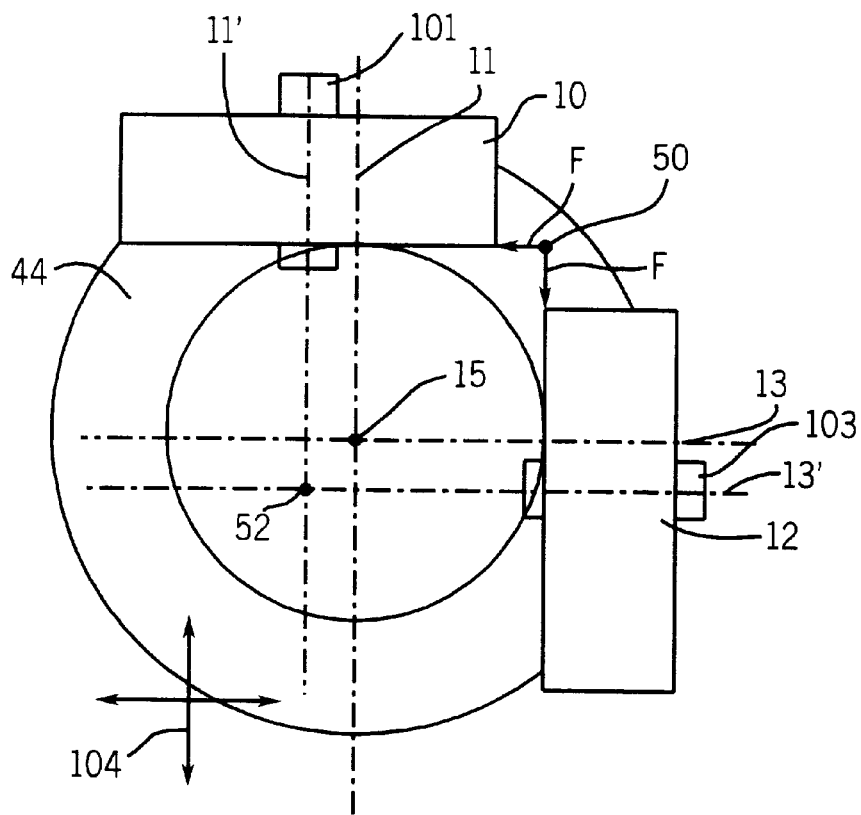
FIG. 3 is a schematic diagram similar to FIG. 2, albeit with the cameras mounted so as to be laterally shifted away from each other.

Referring now to the drawings, wherein like reference characters represent corresponding elements throughout the several views, and more specifically referring to FIG. 2, therein is illustrated a prior art SPECT system including first and second gamma cameras 10 and 12 mounted on a gantry 44 for rotation about an axis 15. Camera 10 is centered on a camera axis 11 while camera 12 is centered on a camera axis 13, the axis 11 and 13 intersecting at rotation axis 15. Adjacent corners 26 and 28 of cameras 10 and 12, respectively, contact at a point 50 when cameras 10 and 12 are configured in the L mode. A patient support table 30 is positioned within an imaging area 54 which is in the field of view of each of cameras 10 and 12.

Referring to FIG. 3, according to the present invention, instead of mounting cameras 10 and 12 in the fashion illustrated in FIG. 2 where camera axis 11 and 13 intersect axis 15, cameras 10 and 12 are mounted to the gantry in laterally offset positions from point 50 such that modified camera axis 11' and 13' intersect at an intersection point 52 which is further away from each of cameras 10 and 12 than is axis 15. While maintaining cameras 10 and 12 at their radial positions with respect to axis 15, camera 10 is moved laterally away from camera 12 a distance F while camera 12 is moved laterally away from camera 10 an equal distance F. As illustrated in FIG. 3, camera 10 is moved a distance F to the left while camera 12 is moved a distance F downward. Once positioned as illustrated in FIG. 3, cameras 10 and 12 are each mounted to gantry 44 via separate radial slides 101, 103, respectively. Each of slides 101 and 103 allows an associated camera 10 or 12 to be move radially with respect to axis 15.

Figure 4:
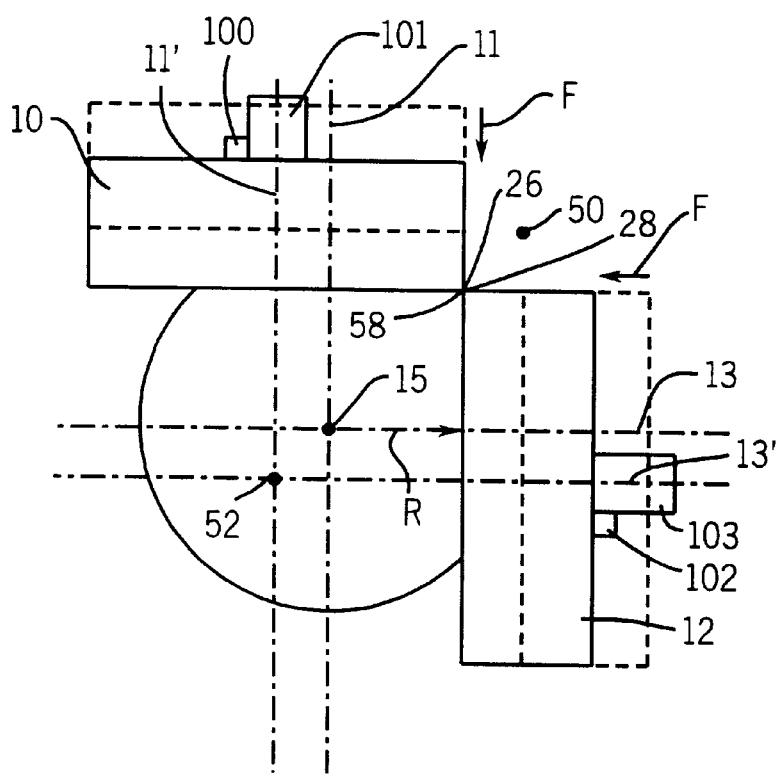
FIG. 4 is a schematic diagram illustrating how, when the cameras of FIG. 3 are offset the cameras can be moved radially inwardly toward an imaging axis to reduce an effective radius of rotation.

Referring now to FIGS. 3 and 4, with cameras 10 and 12 mounted as illustrated in FIG. 3, cameras 10 and 12 can be moved radially inwardly toward axis 15 by a distance F when cameras 10 and 12 are in the L mode. Locking mechanisms 100 and 102 are provided on each of cameras 10 and 12, respectively, to lock the cameras in the radially inward and L positions. Any locking mechanism known in the art may be used for this purpose. When moved inwardly a distance F, adjacent camera corners 26 and 28 again touch, this time at a point 58 which is closer than point 50 (see FIG. 4) to axis 15.

Comparing FIGS. 2 and 4, the distance between axis 15 and each of cameras 10 and 12 represented by the symbol R in FIG. 2 has been reduced to (R−F) in FIG. 4. In the case of FIG. 4, Equation 1 above can be rewritten as follows:

$$d = \frac{(R-F-r)}{\cos(\gamma/2)} \qquad \text{Eq. 2}$$

According to Equation 2, when cameras 10 and 12 are mounted to gantry 44 with lateral offsets of distance F, the table travel distance d required to accommodate a relatively small patient having a chest diameter of r is substantially reduced. For example, assuming again that the initial radius R in FIG. 2 is 304 millimeters, the minimum chest diameter r is 200 millimeters and that angle γ is 90°, if distance F is 40 millimeters, according to Equation 2, the table travel distance required to accommodate the relatively small patient would be 90 mm. Clearly 90 mm is a much smaller travel distance than a 147 mm which would be required with the system of FIG. 2 where no lateral offset is provided.

Figure 5:
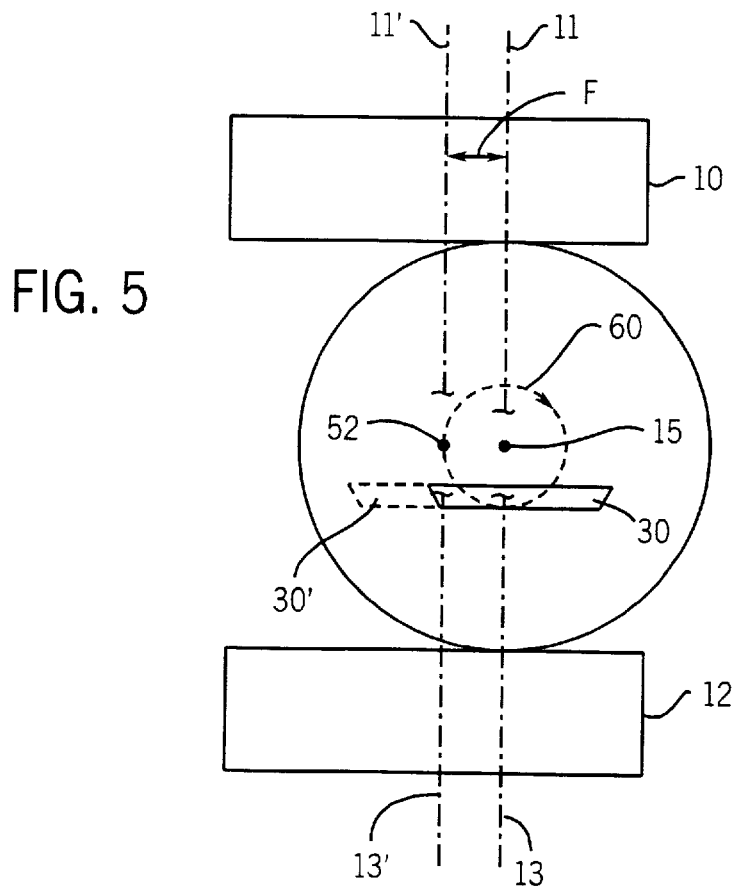
FIG. 5 is a schematic diagram illustrating the offset cameras of FIG. 3 when the cameras are positioned in the H mode.

Referring now to FIG. 5, where cameras 10 and 12 are mounted to gantry 44 and as described above with respect to FIG. 4 with lateral offsets F, when cameras 10 and 12 are reconfigured so as to be in the H mode (e.g. camera 12 is moved radially in a clockwise direction with respect to camera 10), offset camera axis 11' and 13' will be coaxial and will be laterally shifted with respect to the camera axis 11 and 13 of a system such as the one illustrated in FIG. 2. In this case, for body or brain SPECT cameras 10 and 12 are opposed and are rotated through 180° to acquire SPECT data. If a patient is centered within the gantry so that imaging axis 15 passes directly through the organ to be imaged, the Asymmetric mounted cameras 10,12 provide a field of view which, where each camera has a 540 mm field of view, is 460 fully imaged and 620 mm with partial imaging. This arrangement allows studies of the brain and small bodies.

To provide an untruncated SPECT field of view, table 30 can be moved laterally a distance F in the same direction which camera 10 was shifted prior to mounting (i.e. in FIG. 5, to the left). The shifted table is shown in dotted lines and is referenced by numeral 30'. Then, with an axis through intersection point 52 passing through the organ to be imaged, the untruncated field of view can be acquired by using lateral and vertical table motion to move the patient in a radius of 40 mm as cameras 10 and 12 rotate so that the center of the organ to be imaged is kept at the center of both detectors. The radius of motion is identified by arc 60 in FIG. 5.

Figure 6:
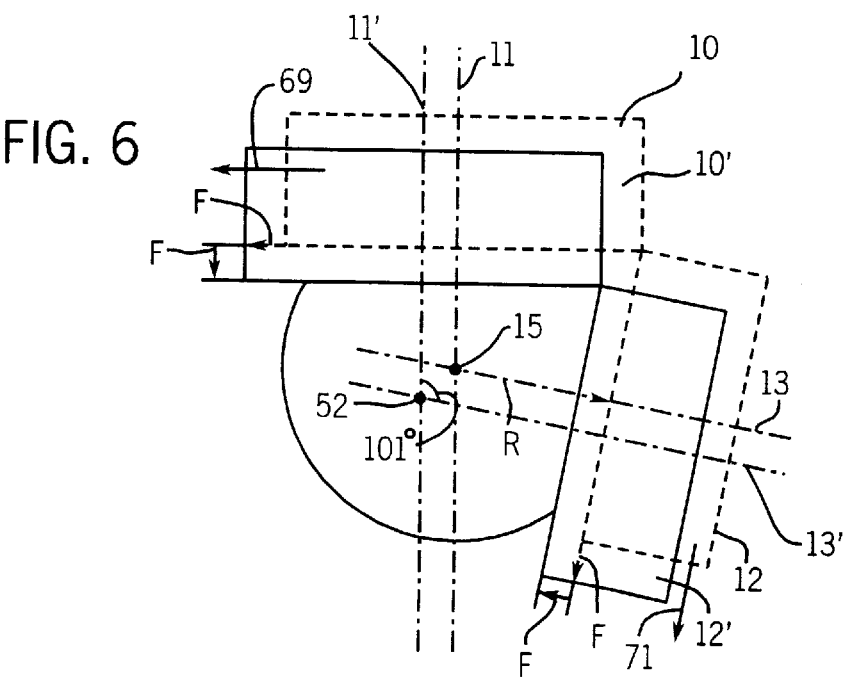
FIG. 6 is a schematic diagram similar to FIG. 4, albeit where an angle between camera axis is 101° instead of 90°.

It should be understood that the methods and apparatuses described above are only exemplary and do not limit the scope of the invention, and that various modifications could be made by those skilled in the art that would fall under the scope of the invention. For example, while the lateral offset camera configuration is illustrated above with respect to an L mode camera configuration wherein the camera axis 11 and 13 form a right angle, clearly, the invention is also applicable to the situation wherein other camera axis are provided. For example, referring to FIG. 6, cameras 10 and 12 as they would appear in a prior art L mode wherein camera axises 11 and 13 define a 101 ° imaging angle are illustrated in phantom. Fixed radius R is identified. According to the present invention, cameras 10 and 12 are both laterally shifted prior to mounting the cameras to a gantry via radial slides (not illustrated). To this end, as illustrated in FIG. 6, camera 10 is laterally shifted away from camera 12 along the direction illustrated by arrow 69 a distance F while camera 12 is laterally shifted away from camera 10 a distance F in the direction indicated by arrow 71. Cameras 10 and 12 are then securely mounted via radial slides to the gantry.

Prior to imaging in the L mode, camera 10 can be moved radially inwardly from its outer most radial position a distance F toward axis 15. Camera 10's final position is illustrated by numeral 10'. Similarly, camera 12 is moved radially inwardly from its outer most radial position a distance F toward axis 15 and its final resting position is indicated by numeral 12'. In this case, new camera axes 11' and 13' intersect at an intersection point 52 which is further away from each of cameras 10' and 12' than is imaging axis 15.

Equation 2 above can be used to identify the table movement required to accommodate a 200 mm chest in the 101° L mode. To this end, assuming an initial fixed radius of rotation R of 267.5 mm (the initial fixed radius R is less when cameras 10 and 12 are configured in a 101° L mode as opposed to a 90° L mode), a required minimum radius r of 200 mm and a precise 101° angle, according to Equation 2, where F is 0, required table movement d would be 107 mm. According to Equation 2, where distance F is 40 mm, required table movement d is reduced to 43 mm.

In addition, offset distance F may be any value within a reasonable range (e.g. 1 to 60 mm). Moreover, the invention may be used with a moveable gantry/stationary table system to minimize required degrees of gantry movement. To this end, referring again to FIG. 3, gantry 44 may be movable in two dimensions illustrated by crossed arrow 104".

To apprise the public of the scope of this invention, we make the following claims.

We claim:

1. An imaging system for generating SPECT images, the system for use with a table positionable to support an object to be imaged within an imaging area, the table capable of vertical and lateral movement to position the object within the imaging area in required positions relative to SPECT cameras, the system for minimizing the degree of table movement necessary to achieve the required positions, the system comprising:

a gantry formed about a rotation axis through the imaging area; and first and second cameras having first and second camera axis which pass through first and second camera fields of view, respectively;

wherein, each of the first and second cameras is mounted to the gantry for radial movement relative to the rotation axis and for rotational movement about the rotation axis, the cameras positionable on the gantry in at least an opposing position wherein the second camera opposes the first and the camera fields of view are aligned and an L position wherein the first and second camera axis intersect at an intersection point and essentially form an L and neither camera blocks the field of view of the other camera, the cameras mounted such that when in the L position the camera axis intersection point is further than the rotation axis from each of the cameras thereby enabling the cameras to be moved radially inward while still maintaining identical distances from the rotation axis to reduce the distance between the rotation axis and each of the cameras.

2. The system of claim 1 wherein, when in the L position the first and second camera axis form a 90° angle.

3. The system of claim 1 wherein, when in the L position the first and second camera axis form an angle greater than 90°.

4. The system of claim 1 wherein, prior to imaging, when in the L position with the cameras moved into a position in which each camera is radially inward as far as possible while still maintaining identical distances between each camera and the rotation axis, a locking mechanism is provided to maintain the cameras in the L position.

5. The system of claim 4 wherein, when in the opposing position the cameras can be moved radially with respect to the rotation axis.

6. The system of claim 5 wherein the table can be moved independently in horizontal and vertical axis so that non-circular objects can be brought close to both cameras.

7. An imaging system for generating SPECT images, the system for use with a table and gantry, the table positionable to support an object to be imaged within an imaging area, the gantry formed about a rotation axis through the imaging area, the table capable of vertical movement and the gantry capable of lateral movement to position the object within the imaging area in required positions relative to SPECT cameras, the system for minimizing the degree of table and gantry movement necessary to achieve the required positions, the system comprising:

first and second cameras having first and second camera axis which pass through first and second camera fields of view, respectively;

wherein, each of the first and second cameras is mounted to the gantry for radial movement relative to the rotation axis and for rotational movement about the rotation axis, the cameras positionible on the gantry in at least an opposing position wherein the second camera opposes the first and the camera field of view are aligned and an L position wherein the first and second camera axis intersect at an intersection point and essentially form an L and neither camera blocks the field of view of the other camera, the cameras mounted such that when in the L position the camera axis intersection point is further than the rotation axis from each of the cameras thereby enabling the cameras to be moved radially inward while still maintaining identical distances from the rotation axis to reduce the distance between the rotation axis and each of the cameras.

8. The system of claim 7 wherein, when in the L position the first and second camera axis form a 90° angle.

9. The system of claim 7 wherein, when in the L position the first and second camera axis form an angle greater than 90°.

10. The system of claim 7 wherein, prior to imaging, when in the L position with the cameras moved into a position in which each camera is radially inward as far as possible while still maintaining identical distances between each camera and the rotation axis, a locking mechanism is provided to maintain the cameras in the L position.

11. The system of claim 10 wherein, when in the opposing position the cameras can be moved radially with respect to the rotation axis.

12. The system of claim 11 wherein the gantry can be moved independently along a horizontal axis and the table can be moved independently along the vertical axis so that non-circular objects can be brought close to both cameras.

13. An imaging system for generating images of an object within an imaging area, the system comprising:

a support formed about a rotation axis through the imaging area; and first and second cameras having first and second camera axis which pass through first and second camera fields of view, respectively, each of the first and second cameras is mounted to the support for movement which is limited to radial movement relative to the rotation axis and rotational movement about the rotation axis, the cameras positionable in at least an opposing position wherein the second camera opposes the first and the camera field of view are aligned and an L position wherein the first and second camera axis intersect at an intersection point and essentially form an L and neither camera blocks the field of view of the other camera, the cameras mounted such that when in the L position the camera axis intersection point is further than the rotation axis from each of the cameras.

14. The system of claim 13 wherein the support is a gantry.

15. The system of claim 13 wherein, when in the L position the first and second camera axis form a 90° angle.

16. The system of claim 13 wherein, when in the L position the first and second camera axis form an angle greater than 90°.

17. The system of claim 14 further including a table for supporting the object within the imaging area, at least one of the table and gantry moveable with respect to the other of the table and gantry for modifying the position of the object within the imaging area.

18. The system of claim 17 wherein the table is moveable in a first direction and the gantry is moveable in a second direction and the first and second directions are perpendicular.

19. The system of claim 17 wherein the table is moveable in first and second directions to change the position of the object with respect to the cameras and wherein the second direction is perpendicular to the first.

20. The system of claim 14 wherein the gantry is moveable in first and second directions to change the position of the object with respect to the cameras and wherein the second direction is perpendicular to the first.

* * * * *